United States Patent [19]

Sevrain et al.

[11] Patent Number: 4,926,879
[45] Date of Patent: May 22, 1990

[54] ELECTRO-TACTILE STIMULATOR

[75] Inventors: Christophe Jean-Paul Sevrain, Fitchburg, Wis.; Heather R. Schramm, Minneapolis, Minn.; Daniel G. Schmidt, Dane, Wis.; Paul S. Hooper, Stoughton, Wis.; Mary P. Thomas, Madison, Wis.

[73] Assignee: Sevrain-Tech, Inc., Madison, Wis.

[21] Appl. No.: 406,192

[22] Filed: Sep. 12, 1989

Related U.S. Application Data

[63] Continuation-in-part of Ser. No. 205,919, Jun. 13, 1988, abandoned.

[51] Int. Cl.⁵ ............................ A61N 1/02; A61N 1/36
[52] U.S. Cl. .................................... 128/798; 128/421; 340/407
[58] Field of Search ............... 128/783, 798, 799, 802, 128/419 R, 419 F, 420 R, 420.5, 421, 422, 423 R, 642, 639, 784; 340/407

[56] References Cited

U.S. PATENT DOCUMENTS

| | | | |
|---|---|---|---|
| 2,327,222 | 8/1943 | Sell | 35/1 |
| 2,703,344 | 3/1955 | Anderson | 179/701 |
| 3,108,268 | 10/1963 | Uttal | 128/783 X |
| 3,562,408 | 2/1971 | Collins | 178/5.2 |
| 3,592,965 | 7/1971 | Diaz | 178/6.8 |
| 3,594,787 | 7/1971 | Ickes | 340/407 |
| 3,612,061 | 10/1971 | Collins et al. | 128/799 |
| 3,628,193 | 12/1971 | Collins | 3/1 |
| 3,721,246 | 3/1973 | Landis | 128/783 |
| 3,766,311 | 10/1973 | Boll | 178/6 |
| 3,848,608 | 11/1974 | Leonard | 128/419 R |
| 3,893,462 | 7/1975 | Manning | 128/421 |
| 3,924,641 | 12/1975 | Weiss | 128/421 X |
| 4,067,342 | 1/1978 | Burton | 128/798 |
| 4,167,189 | 9/1979 | Tachi et al. | 128/421 |
| 4,390,756 | 6/1983 | Hoffman et al. | 128/420.5 |
| 4,514,589 | 4/1985 | Aldinger et al. | 128/784 X |
| 4,551,149 | 11/1985 | Sciarra | 623/4 |
| 4,619,266 | 10/1986 | Hodgson | 128/639 |

FOREIGN PATENT DOCUMENTS

8707825  12/1987  World Int. Prop. O. .......... 128/642

OTHER PUBLICATIONS

Mason et al., "Pain Sensations . . . Stimulation", IEEE Trans. Biomed. Eng., vol. 23, No. 5, pp. 405–409, Sep. 1976, (copy 340/407).
Kume et al., "Perception of Dot Matrix . . . ", Med. & Biol. Eng. & Comput., 1986, 24, 651–654, (copy 128/419 R).

Primary Examiner—Lee S. Cohen
Attorney, Agent, or Firm—Quarles & Brady

[57] ABSTRACT

A device for electrically stimulating the skin in response to an electrical signal includes a flexible substrate on one surface of which is formed an electrically conductive pattern having a number of electrodes. Each of the electrodes is coated with a layer of a corrosion resistive material, such as titanium. An insulating layer extends over this surface of the substrate and has apertures therethrough aligned with the electrodes. A conductive ground plane layer is then applied over the insulating layer and also has apertures therethrough which are aligned with each of the electrodes. The stimulator is placed against the user so that the coated electrodes are in contact with the skin. In response to the received electrical signal, each electrode is sequentially stimulated by a negative and a positive electrical pulse. The negative and positive pulses have magnitudes which differ in a predetermined relationship so that the pH of the skin adjacent to the electrode is not altered substantially by the electrical stimulation.

21 Claims, 5 Drawing Sheets

ELECTRO-TACTILE STIMULATOR

This application is a continuation-in-part of application Ser. No. 205,919, filed June 13, 1988, now abandoned.

BACKGROUND OF THE INVENTION

The present invention is related to devices for stimulating the skin in response to an external stimulus in order to aid a person who is sensorially impaired with respect to that external stimulus.

Cutaneous signaling devices which respond to sound or light, are well known aids to persons having impaired senses of hearing or sight. For example, previous auditory systems, such as that disclosed in U.S. Pat. No. 2,702,344, utilized a microphone to pick up sound which was then electrically divided into signals corresponding to various frequency bands within the audio spectrum. The magnitude of the signal for each band was employed to stimulate different regions of the skin of a hearing impaired individual. One type of such stimulation involved energizing separate electromagnetic solenoids which caused a plunger to impact the skin. With proper training the hearing impaired individual was able to recognize different sounds by the patterns of impact of the solenoid stimulator array.

Another type of stimulator employed a pattern of electrodes each having an electrical current applied to it in response to sound in a different one of the audio bands. Often such devices applied the stimulating current as a pair of pulses of opposite polarity and equal magnitude. These stimulators were current controlled so that the voltage could increase as the user's skin resistance increased. The magnitude of the current applied to a given electrode corresponded to the intensity of the sound in the respective audio band. This enabled the individual to perceive not only sound within each of the bands, but the sound's relative intensity. Similar electrode stimulation devices were created for the visually impaired individual with two dimensional stimulator arrays responding to picture elements of a video image.

The major drawback to the previous cutaneous stimulator systems was skin irritation produced after a relatively short period of usage (e.g. on the order of a few minutes). Skin reddening was quite common and even burns have been reported with the electrical stimulation. Therefore, before such cutaneous stimulators can effectively be used as an aid to a visually or hearing impaired individual, a solution to the skin irritation problem must be found to enable their continuous use for periods of practical duration.

SUMMARY OF THE INVENTION

A cutaneous stimulator has a thin flexible substrate with a surface on which is formed a printed circuit pattern. The pattern comprises a plurality of electrodes and conductors connected to the electrodes. An insulating layer is contiguous to the surface of the substrate and has a plurality of apertures, each one being aligned with one of the electrodes. An electrically conductive layer, which can be formed of a plastic that is impregnated with a conductive material, is contiguous with the insulating layer and acts as a ground plane electrode. The conductive layer has a plurality of apertures therethrough, each one of which being aligned with a different one of the electrodes. The electrodes of the stimulator extend through the insulating and conductive layers so that when the stimulator is worn by the user, the electrodes will be in electrical contact with the skin.

The stimulator is used with a circuit which applies electricity selectively between various ones of said electrodes and the conductive ground plane layer to stimulate the skin of the individual wearing the stimulator. The electricity is applied to each of said electrodes in a manner such that it will not substantially affect the pH of the skin in the region that contacts the stimulator. This stimulation technique is referred to as being pH balanced, rather that electrically balanced as was the case with previous systems.

In the preferred embodiment, this pH balancing is accomplished by regulating the amount of electrical charge applied to the electrodes. Specifically, the application of electricity to an electrode comprises a sequence of negative charge and positive charge pulses having voltages between ±20 volts. The negative charge has a greater magnitude than the positive charge. The degree of imbalance between the negative and positive charge pulses is chosen so that the pH of the skin beneath the stimulator will remain substantially unchanged as a result of the stimulation.

A general object of the present invention is to provide an apparatus for applying stimulating electrical pulses to the skin.

A specific object is to provide an electrode structure for this apparatus which can conform to the contour of various portions of the body and be relatively flexible so that it is comfortable to wear.

Another object of the present invention is to provide such a cutaneous stimulator that does not produce substantial skin irritation with continued electrical stimulation.

Yet another object of the present invention is to provide electrical cutaneous stimulation by regulating the charge applied to an electrode so that the pH of the skin beneath the electrode and the conductive ground plane layer remains substantially unchanged due to the stimulation.

A further object of the present invention is to sequentially apply a positive and a negative charge to the electrode for each stimulation. The amount of positive charge has a predetermined relationship to the the amount of negative charge so that the pH of the skin remains substantially unchanged due to the application of the two charges.

DETAILED DESCRIPTION OF THE PRESENT INVENTION

The present inventors believe that the skin irritation after continued use of previous electro-stimulator devices resulted from a change in the pH of the skin due to the stimulation. Although previous electro-stimulator devices often applied both negative and positive currents of equal absolute magnitudes in an attempt to create electrically balanced stimulation, irritation still resulted. The present inventors have discovered that creating electrical pulses equally balanced by either current or voltage control, still produces a net change in the pH of the skin being stimulated.

Figure 9:
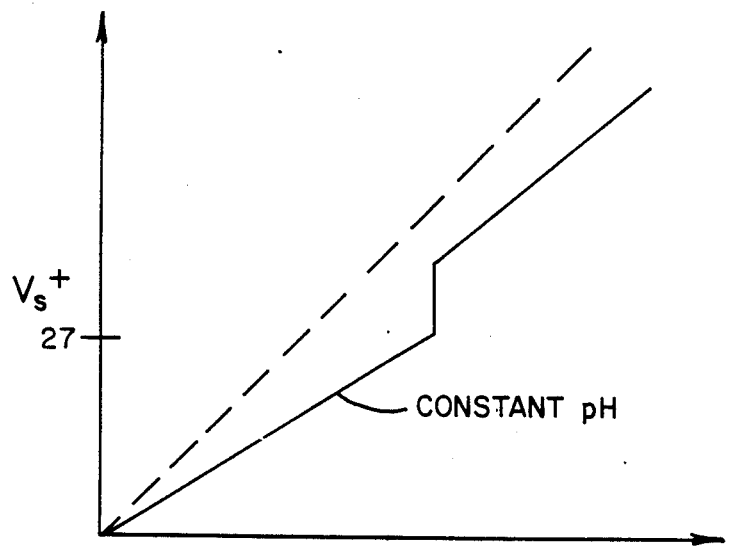
FIG. 9 is a graph illustrating the relationship between the magnitude of the negative and positive electrical stimulation pulses to maintain a constant pH of the individual's skin.

After further research into the correspondence between the magnitude of the negative and positive electrical skin stimuli and pH change, it was discovered that a specific imbalance of the opposite polarity pulses produced skin stimulation without a pH change and without severe skin irritation. The degree of this imbalance of the negative and positive pulses is a function of the stimulating electrode material. For, example, the constant pH relationship between the pulse magnitudes for titanium is graphically illustrated in FIG. 9. The vertical axis of the graph represents the magnitude $Vs^+$ of the positive voltage stimulation pulse and the horizontal axis represents the magnitude $Vs^-$ of the negative voltage stimulation pulse. The dashed line of the graph corresponds to points where the two pulses would be of equal magnitude. The inventors' research disclosed that the voltage magnitude of the negative and positive pulses applied to the stimulating electrode must be specifically imbalanced in order not to affect the pH of the stimulated skin. The relationship between the voltage magnitude of the negative and positive pulses to achieve this is represented by the solid curve of the graph. This relationship appears to be independent of pulse width, as well as the salt concentration and other characteristics of the user's skin, but is dependant upon the material of the electrode which contacts the skin.

Portions of the curve can be approximated by linear equations. For example, the lower linear portion of the titanium electrode constant pH curve, where the value of $Vs^+$ is less than approximately 27 volts, is represented by the linear equation $|Vs^-| = 1.3\ Vs^+ + 1.2$. The upper section of the pH curve, where $Vs^+$ is slightly above 27 volts, is represented by the equation: $|Vs^-| + 1.2\ Vs^+ + 2.6$.
Electrode materials other than titanium have similar constant pH curves and stimulation voltage relationships.

Investigation of the shortcomings of previous skin stimulation devices found another problem with the ones employing current control of the pulses. If the electrodes of the device make poor contact with the user's skin, the current flow is concentrated into relatively small areas of contact. This creates a large current density in these areas of the skin which results in irritation. However, the present inventors found that by using charge control of the electrical pulses, the adverse effects due to poor electrode contact were reduced.

Figure 1:
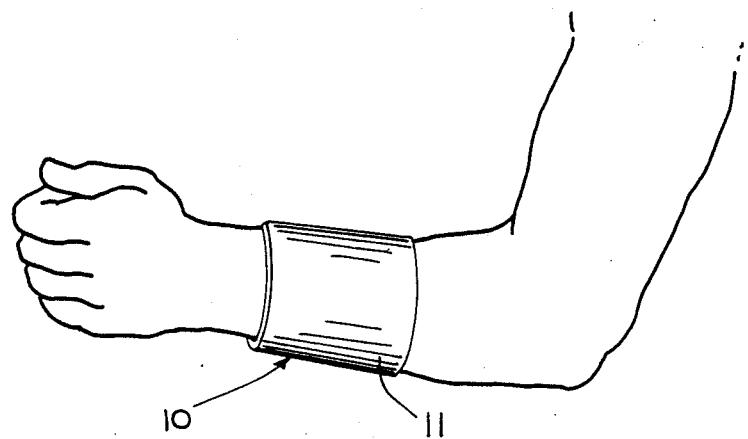
FIG. 1 illustrates a cutaneous stimulator worn about the arm of an individual.

As a result of this research, an electro-tactile auditory system was developed which stimulates the skin in response to sounds. The skin is stimulated by pairs of negative and positive electrical charge pulses having magnitudes which correspond to the intensity of the ambient sound. The relative magnitudes of the charges of each pair are regulated to create the electrical imbalance specified by the graph of FIG. 9. As a consequence, the present electro-tactile stimulator can be used for significant periods of time without substantial skin irritation. As illustrated in FIG. 1, this electro-tactile auditory system 10 includes a cutaneous stimulator 11 in the form of a band which is wrapped around the forearm of a user. The stimulator band has an adjustable fastener at its ends to tightly hold the stimulator around the arm. The system responds to sounds by stimulating the skin of the user at various location around the arm thereby enabling the individual to discern different sounds. Such a device is particularly useful for hearing impaired individuals, especially as a supplement to lip reading. The cutaneous stimulator 11 can be placed against other parts of the body, such as the forehead, abdomen or back as long as these regions are sufficiently sensitive to discriminate between different closely spaced stimuli.

Figure 2:
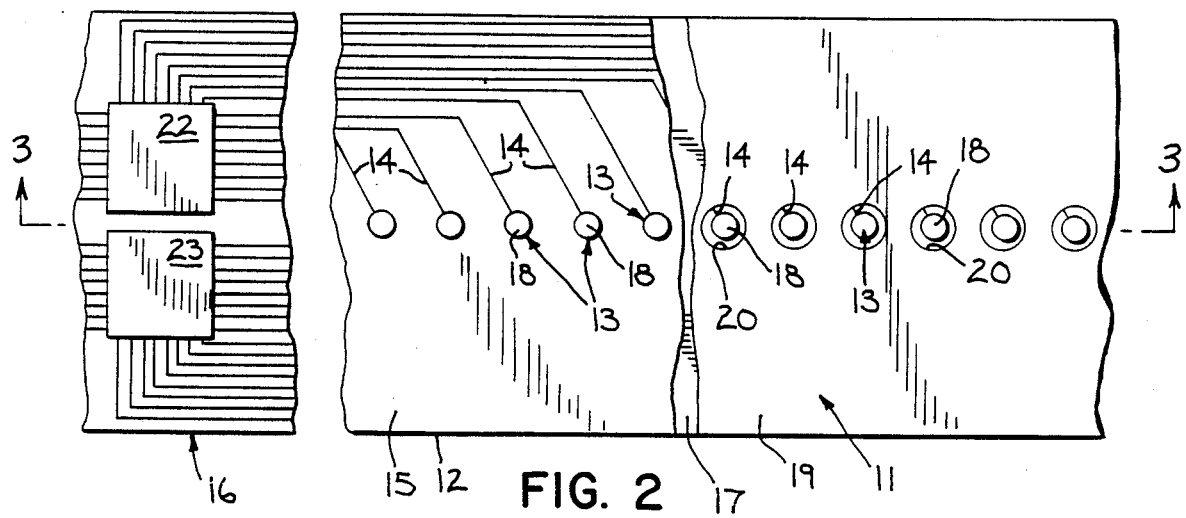
FIG. 2 is a partial cut-away plane view of the present stimulator.
Figure 3:
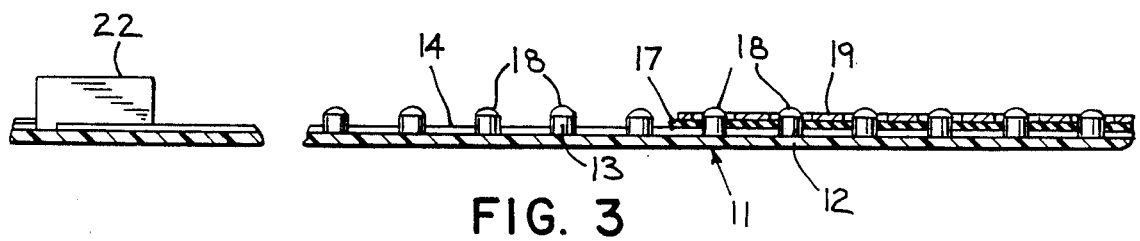
FIG. 3 is a cross section view taken longitudinally through the stimulator along line 3—3 of FIG. 2.

As shown in FIGS. 2 and 3, the cutaneous stimulator 11 is formed on a substrate 12 of a flexible, electrically insulative material, for example a polyimide plastic such as Kapton (trademark of E. I. du Pont de Nemours & Company). The substrate is approximately 50 microns thick. (The thickness of the stimulator 11 and its component layers has been exaggerated in FIG. 3 for illustration purposes). One major surface 15 of the substrate 12 initially is coated with a layer of a conductive material, such as copper. Using conventional photolithographic techniques, a conductive pattern of electrodes 13 and electrical conductors 14 is produced on the substrate 12 from the conductive material layer. Each of the electrodes 13 is connected to one of the conductors 14 which extends from the electrode to an end section 16 of the arm band-like stimulator 11.

In the exemplary embodiment, the pattern of electrodes forms a linear array of thirty-two electrodes 13 along the longitudinal axis of the substrate 12. The electrodes are each approximately two millimeters in diameter and are spaced on five millimeter centers, although the size and spacing will vary depending upon the sensitivity of the part of the body on which the stimulator 11 will be worn. A layer 18 of a corrosion resistant conductive material, such as titanium, silver, gold, graphite, or platinum, is applied to the exposed surface of each of the electrodes 13. For example, disks of titanium foil can be cemented to the electrodes 13 by a conductive epoxy.

Alternatively, the layer 18 can be formed of a dielectric material, such as niobium oxide, titanium oxide, tantalum pentoxide, or another metallic oxide, to form a capacitive stimulator rather than one employing direct electrical skin contact. With this capacitive for of the present stimulator, electricity is conducted by ions in the skin migrating to the surface of the dielectric layer instead of being conducted by electrochemical reaction which occurs when electricity is applied by direct skin contact with conductive electrodes. This alternative construction does not require bipolar electrical stimulation pulses with predefined magnitude relationships to avoid skin irritation, since skin irritating pH changes are caused by electrochemical reactions. Electrode corrosion problems are also minimized. The ground plane electrode layer also can be covered by a dielectric material to avoid skin pH changes.

A thin flexible layer 17 of insulating material is contiguous with and adheres to the upper surface 15 of the substrate 12. The insulating layer 17 extends over the conductors 14 and has a series of apertures aligned with and extending around each electrode 13. A ground plane electrode layer 19 is contiguous with the insulating layer 17 and is approximately 50 to 100 microns thick. The ground plane electrode layer 19 is formed by a sheet of a conductive polyimide, such as Kapton XC (trademark E. I. du Pont de Nemours & Company) which is adhesively applied to the insulating layer 17. The ground plane electrode layer 19 has a series of apertures 20 therethrough, with each one being aligned with and slightly larger than one of the electrodes 13 so that the ground plane electrode layer 19 is electrically isolated from the electrode and the conductive layer 18. Alternatively, the ground plane electrode layer 19 car be formed by screen printing graphite onto the exposed surface of the insulating layer 17. The combination of the electrodes 13 and their corrosion resistant layers 18 form the array of stimulating electrodes having a concentric ground plane electrode.

The conductors 14 extend from each of the electrode 13 to one of two integrated circuits 22 and 23 mounted on an end portion 16 of the stimulator 11. The integrated circuits 22 and 23 contain the electronic circuitry for processing the audio signal and applying a stimulating electrical charge sequentially between each of the electrodes 13 and the ground plane 19. These circuits are formed in surface mounted devices that are affixed directly to the substrate 12 thereby minimizing the thickness of the entire stimulator 11. The integrated circuits 22 and 23 are shown positioned on the upper surface 15 of the substrate 12.

Figure 10:
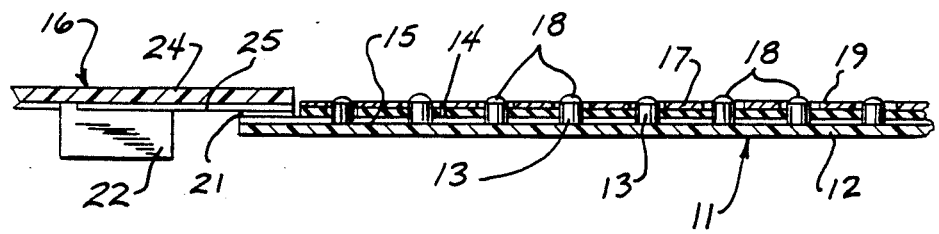
FIG. 10 is a cross section view taken longitudinally through another embodiment of the novel stimulator.

Alternatively, since the upper surface 15 is worn toward the skin of the user, the integrated circuits 22 and 23 may be placed on the underside of the substrate 12 so as to be away from the skin. For one implementation of this version, the conductors 14 extend to plated-through holes in the substrate 12 in order to make electrical connection with the integrated circuits. FIG. 10 illustrates another implementation of this version of the stimulator. The end section 16 on which the integrated circuits 22 and 23 are mounted comprises a separate substrate 24 having a plurality of electrical conductors 25 formed on one surface. The integrated circuits 22 and 23 are attached to the conductors 25. The two substrates 12 and 24 are overlapped and their electrical conductors 14 and 25 are connected together. For example, a conductive adhesive 21 can be applied between the conductors to provide both a mechanical and an electrical coupling of the two substrates 12 and 24. Specifically a Z-axis interconnect film such as the kind manufactured by Sheldahl Inc. of Northfield, Minn. can be employed as the adhesive. This film has a relatively low resistance in the direction normal to the surface 15 of substrate 12 and a relatively high resistance in the directions parallel to the surface 15. This allows the film to be placed across the entire interface between the two substrates 12 and 24, thereby adhering the substrates as well as the conductors together without shorting the conductors.

Figure 4:
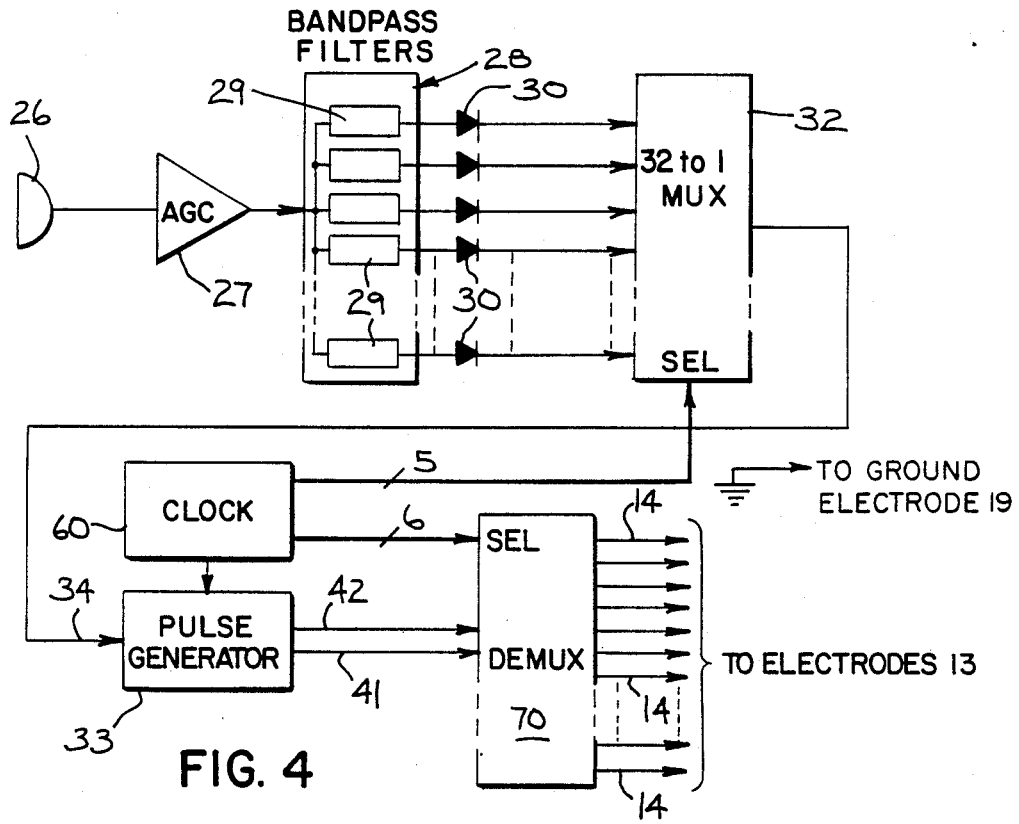
FIG. 4 is a block diagram of the circuitry for driving the cutaneous electrodes when the stimulator is used in an auditory system for the hearing impaired.

FIG. 4 is a block diagram of the electronic circuitry for the electro-tactile auditory system 10, which uses the direct electrode contact stimulator, rather than the capacitive stimulator alternative. As noted above, the direct contact version of the present stimulator requires bi-polar electrical pulse stimulation in which the relative magnitudes of the pulses are controlled to minimize skin irritation. The auditory system 10 includes a microphone 26 which can either be mounted onto the substrate 12, or connected to the substrate by a wire and located elsewhere on the user. The microphone 26 is connected to an input of an automatic gain control amplifier (AGC) 27.

The output of the automatic gain control amplifier 27 is connected to the inputs of an array 28 of thirty-two bandpass filters 29. The array of bandpass filters 28 divides the human voice frequency spectrum of 100 Hz to 8,000 Hz into thirty-two different bands. The division into these bands is done logarithmically in the preferred emdodiment, but half logarithmic or half linear subdivisions also can be employed. The output of each of the bandpass filters 29 is rectified by a separate diode 30 and coupled to an input of a thirty-two to one multiplexer 32. The multiplexer 32, in response to the incrementation of a five bit digital number applied to its selector input (SEL), sequentially connects the output from each of the bandpass filters 29 to the multiplexer output. The selector input (SEL) number for the multiplexer 32 is produced by a clock circuit 60.

The output of the multiplexer 32 is coupled to the input terminal 34 of an pulse generator 33, which converts the low voltage multiplexer output signals into pairs of opposite polarity, higher voltage skin stimulation pulses. Each pulse is approximately 300 microseconds long and has a magnitude which varies within a given range of values depending upon the magnitude of the voltage received from the multiplexer 32. The magnitude of the positive stimulation pulse corresponds to the magnitude of the negative stimulation pulse according to the above linear equations for the given range of values.

Figure 5:
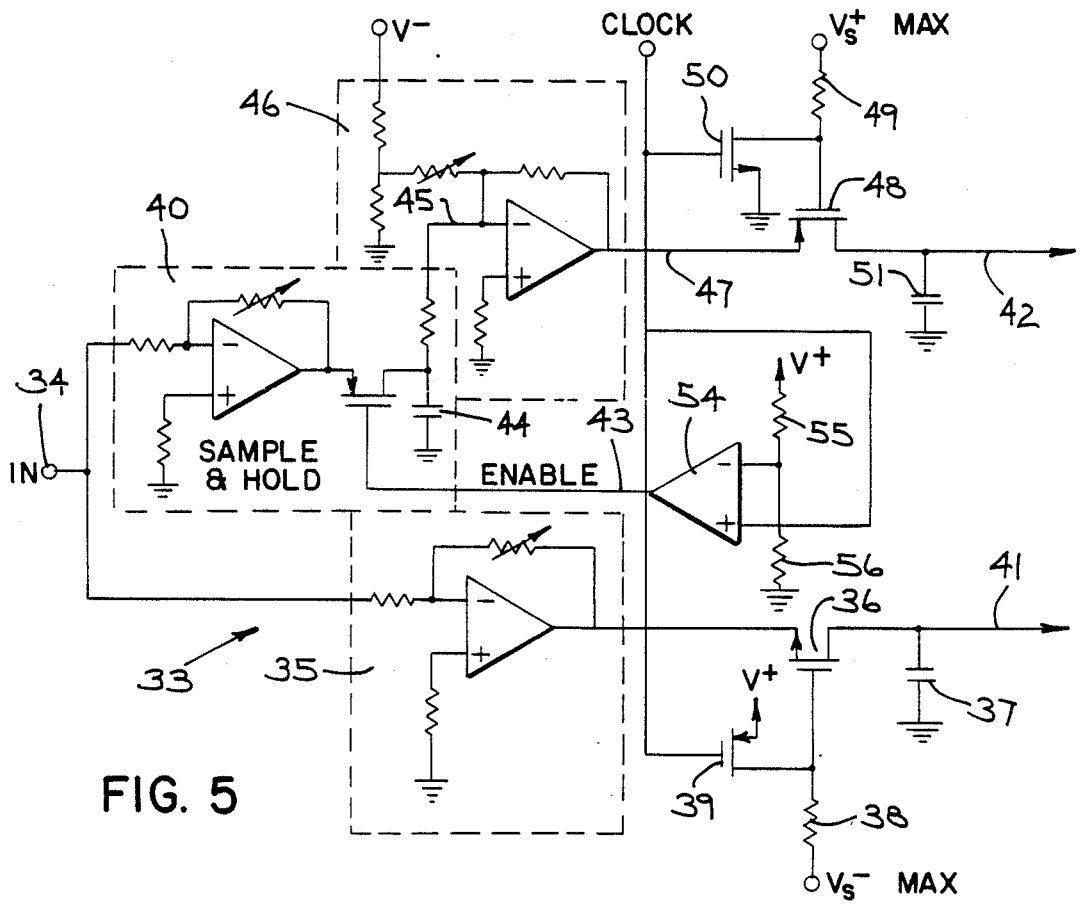
FIG. 5 is a detailed schematic diagram of the pulse generator shown in FIG. 4.

The details of the pulse generator 33 are shown in FIG. 5. The rectified input signal from the multiplexer 32 is applied via terminal 34 to a first amplifier 35, which amplifies and inverts the input signal. The gain of the first amplifier 35 is adjusted to produce the maximum negative stimulation voltage $Vs^-_{max}$ when the input voltage is at its maximum level. In the preferred embodiment, $Vs^-_{max}$ is approximately equal to $-18.3$ volts. The output of the first amplifier 35 is connected to the source electrode of a first N-channel field effect transistor (FET) 36. The gate electrode of FET 36 is coupled to a source of the negative stimulation voltage $Vs^-_{max}$ by a bias resistor 38, and to a source of positive bias potential V+ by a first P-channel switching transistor 39. The conductivity of the first P-channel switching transistor 39 is controlled by a pulse generator clock signal applied to the transistor's gate electrode from the clock circuit 60. The drain electrode of the first N-channel FET 36 is coupled to ground by a first output capacitor 37 and to a first pulse generator output line 41.

The pulse generator input terminal 34 is also coupled to a sample and hold circuit 40, which when activated by a low level signal on an enable line 43, stores the voltage level at the input terminal 34 in a capacitor 44. The output of the sample and hold circuit 40 on line 45 is coupled to a second amplifier 46 having a gain which corresponds to the gain of the first amplifier 35 so that the voltage at its output on line 47 varies according to the above linear equations. Since in the preferred embodiment the value of $Vs^-_{max}$ is approximately $-18.3$ volts, the gain of the second amplifier follows the linear equation for the lower section of the constant pH curve in FIG. 9. However depending upon the desired intensity range for the stimulation charges, the gain can conform to the equation for another section of the curve or to several of the equations.

The output of the second amplifier 46 is coupled to the source electrode of a first P-channel FET 48. The gate electrode of the first P-channel FET 48 is coupled by a bias resistor 49 to a source of the positive stimulation voltage $Vs^+{}_{max}$ and to ground by a first N-channel switching transistor 50. The conductivity of the first N-channel switching transistor 50 is controlled by the pulse generator clock signal applied to the transistor's gate electrode. The drain electrode of the first P-channel FET 48 is coupled to ground by a second output capacitor 51 and to a second pulse generator output line 42.

The pulse generator clock signal is also applied to the non-inverting input of a differential amplifier 54 which has its output coupled to the enable line 43 for the sample and hold circuit 40. The inverting input of the differential amplifier 54 is connected to a voltage divider formed by resistors 55 and 56.

Referring again to FIG. 4, the two output lines 41 and 42 from the pulse generator 33 are coupled to signal inputs of a demultiplexer 70. The demultiplexer 70, in response to a six bit control signal at its selector input (SEL) from the clock circuit 60, couples one of the pulse generator output lines 41 or 42 to one of thirty-two output lines. Each of the demultiplexer output lines is connected by a conductor 14 to one of the thirty-two stimulator electrodes 13.

Figure 7:
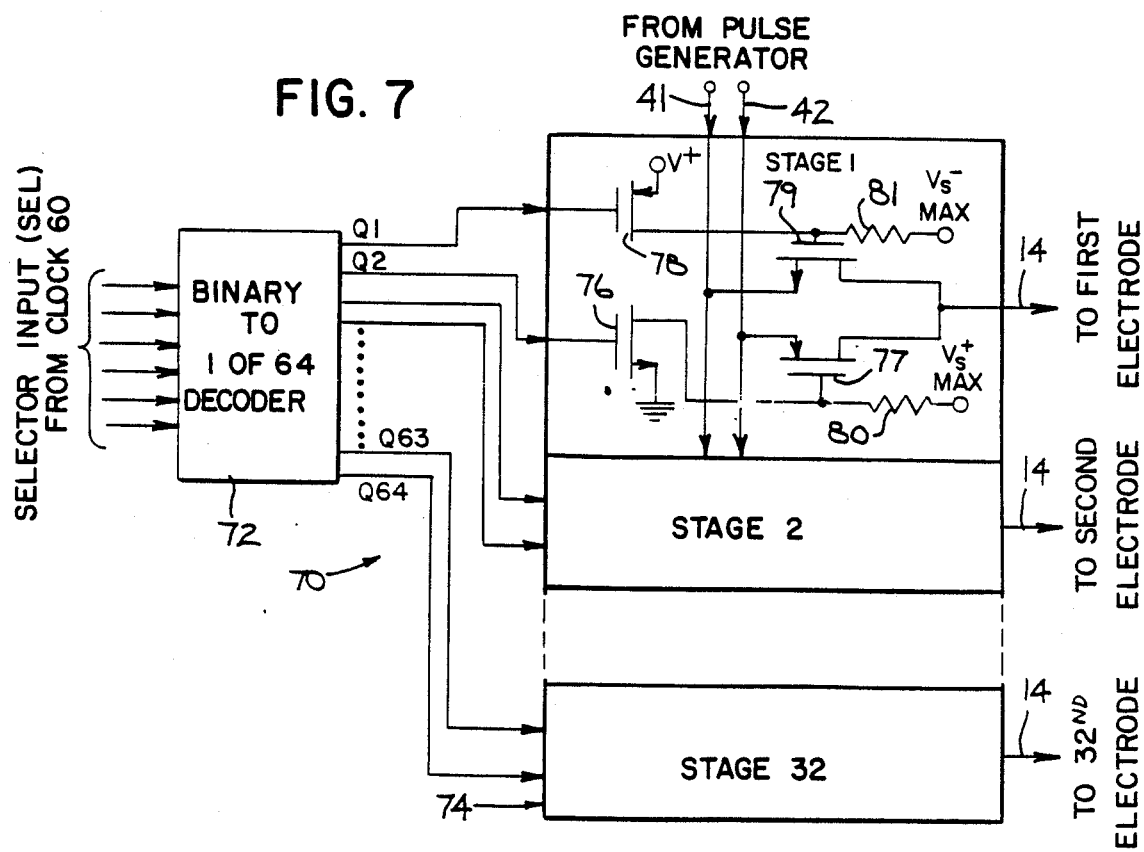
FIG. 7 is a detailed schematic diagram of the demultiplexer shown in FIG. 4.

As shown in detail in FIG. 7, the demultiplexer 70 includes a binary to one of sixty-four decoder 72, which based on the six bit control signal number applied to the demultiplexer selector input (SEL) produces a high logic level signal at one of sixty-four output lines Q1–Q64. The output lines from the decoder 72 are connected to a switching circuit 74 containing thirty-two stages, on a stage for applying the stimulating pulses to each electrode 13. Pairs of consecutive output lines of the decoder 72 are coupled to different stages of the switching circuit 74. For example, the first two decoder output lines, Q1 and Q2, extend to stage 1; the next pair Q3 and Q4 extend to stage 2; and so on. The output lines 41 and 42 of the pulse generator 33 are coupled to each stage of the switching circuit 74.

The circuitry for the first stage of the switching circuit 74 is illustrated in FIG. 7 and other stages are identical to it. The odd numbered decoder output line Q1 for stage 1 is connected to the base of a second P-channel switching transistor 78. The source of switching transistor 78 is connected to the positive voltage source V+ and its drain is coupled to the source of the negative stimulation voltage $Vs^-{}_{max}$ by resistor 81. The base of a second N-channel FET 79 is connected to the drain of transistor 78, and its conductive path couples the first output line 41 of the pulse generator 33 to the first stimulating electrode.

The even numbered decoder output line Q2 for stage 1 is connected to the base of a second N-channel switching transistor 76. The source of this switching transistor 76 is connected to ground and its drain is coupled by resistor 80 to the source of the positive stimulation voltage $Vs^+{}_{max}$. The base of a second P-channel FET 77 is connected to the drain of transistor 76 and its conductive path couples the second output line 42 of the pulse generator 33 to the first stimulating electrode.

Figure 6:
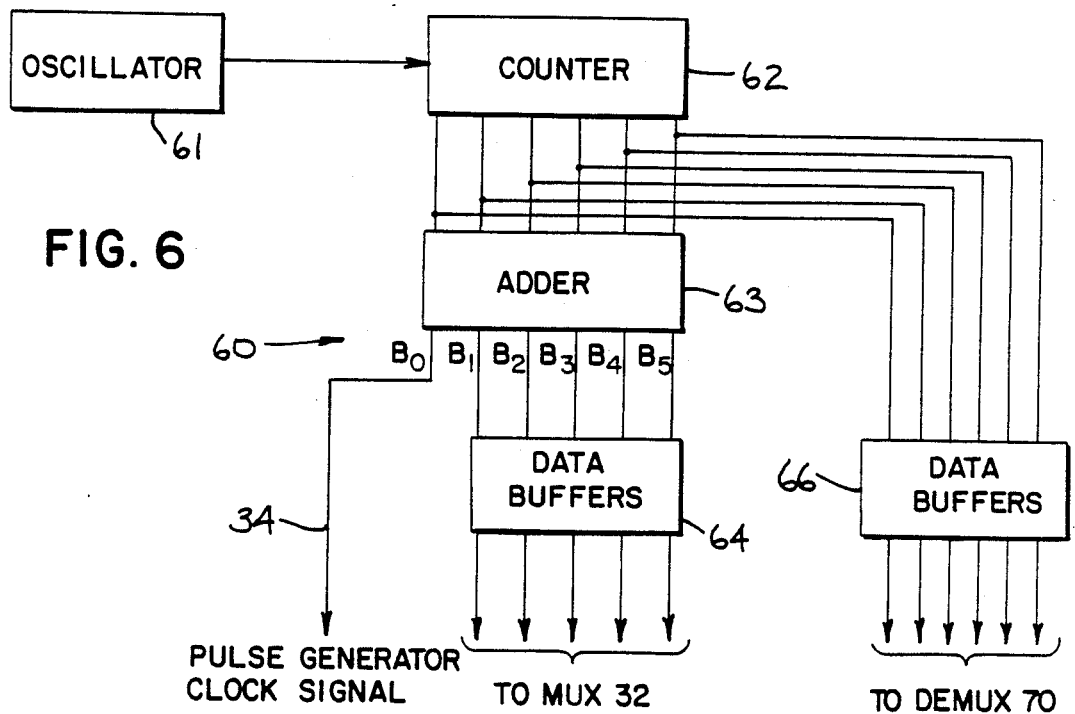
FIG. 6 is a detailed schematic diagram of the clock circuit shown in FIG. 4.

The clock circuit 60 that produces the clock signal for the pulse generator 33 and the selector input signals for multiplexer 32 and demultiplexer 70 is shown in FIG. 6. The clock circuit 60 includes an oscillator 61 which produces a pulsed signal having a frequency of approximately 3.3 kHz. The pulsed signal is coupled to the input of a six bit digital counter 62. The six bit output of the counter 62 is coupled by a first set of data buffers 66 to the selector input (SEL) of the demultiplexer 70. The digital output from the counter 62 also is connected to an adder 63 which adds one to the counter output. The least significant output bit line $B_0$ from the adder 63 is connected to the pulse generator 33 to provide its clock signal. The five most significant output bits $B_1$–$B_5$ from the adder 63 are coupled by a second set of data buffers 64 to the selector input of the multiplexer 32. Since the least significant output bit line $B_0$ from the adder 63 is not coupled to the multiplexer 32, it is clocked at half the rate of the demultiplexer 70. The difference in rates allows the demultiplexer to sequentially apply both a positive and a negative stimulation pulse to an electrode 13 each time a bandpass filter 29 is selected. In addition, due to the adder 63, the multiplexer 32 selects a bandpass filter one oscillator 68 period ahead of when the demultiplexer 70 selects the corresponding stimulation electrode 13. The difference in selection times compensates for a signal propagation delay in the pulse generator 33. The functions and relationships between the various signals from that clock circuit 60 will become apparent in the subsequent description of the operation of the electro-tactile auditory system.

With reference again to the circuitry shown in FIGS. 4 and 5, a sound is converted to an electrical signal by microphone 26 which is amplified by the automatic gain control amplifier 27. The electrical signal representing the detected sound is then applied to the array 28 of bandpass filters 29 to break it into subsignals representing different bands of the audio voice spectrum from 100 Hz to 8,000 Hz. In response to an enable signal from clock 60, the multiplexer 32 sequentially selects the rectified output from each of the bandpass filters 29 and applies it to the input of the pulse generator 33. Initially the first filter of the array 28 is selected.

The selected filter signal, applied to the pulse generator 33, is amplified by the first amplifier 35 which inverts and shifts the input voltage to the proper negative level for stimulating the skin. The amplified signal is applied to the source electrode of the first N-channel FET 36. In response to a low logic level clock signal from clock 60, the first P-channel switching FET 39 is turned on applying a positive potential to the gate electrode of the first N-channel FET 36. When this transistor 36 turns on, the output of the first amplifier 35 is applied to the first output capacitor 37 to produce a negative charge corresponding to the amplitude of the selected audio band signal.

At the same time that the low level clock signal turns on the first N-channel FET 36 to charge its output capacitor 37, the low level clock pulse also produces a negative output from the differential amplifier 54. This negative output causes the sample and hold circuit 40 to store the level of the rectified signal from the selected bandpass filter 29. This voltage level is the same as that which was applied to the input of the first amplifier 35 to generate the negative stimulating charge on the first output capacitor 37.

Figure 8:
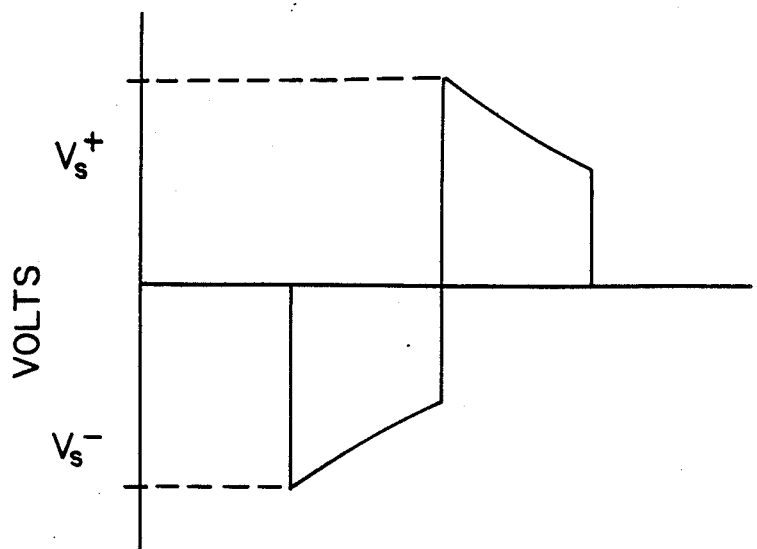
FIG. 8 is a waveform diagram of the electrical signal which stimulates the skin of the individual.

After the first output capacitor 37 charging interval, the pulse generator clock signal goes high turning off the first N-channel FET 36. At this instant the selector signal from the clock circuit 60 steps the demultiplexer 70 to connect the first output line 41 of the pulse generator 33 to the first electrode 13 on the cutaneous stimulator 11. Specifically with reference to FIG. 7, the decoder 72 responds to the new selector signal by activating the first output line Q1, which turns on transistor 78 thereby turning on the second N-channel FET 79. This switching applies the negative charge stored on the first output capacitor 37 to the first stimulator electrode 13. As shown by the waveform in FIG. 8, the negative charge on the first output capacitor 37 then decays via the conductive path through the selected electrode 13 and its surface layer 18 into the skin of the user, returning through the ground plane electrode 19. The width of the negative pulse is approximately 300 microseconds, the period of the clock oscillator 68.

Referring again to FIG. 5, when the negative charge is being applied to the electrode 13, the high level clock signal signal turns on the first N-channel switching FET 50. This clamps the gate electrode of the first P-channel FET 48 to ground, rendering the latter FET conductive. When the first P-channel FET 48 is conductive, the stored potential on capacitor 44 of the sample and hold circuit 40 is amplified by the second amplifier 46 to charge the second output capacitor 51. The gain of the second amplifier 46 corresponds to the gain of first amplifier 35 according the constant skin pH equation given above. Because of the double inversion of the input signal provided by the sample and hold circuit 40 and the second amplifier 46, a positive charge is stored by the second output capacitor 51. It should be noted that while the second output capacitor 51 is charging the first output capacitor 37 is discharging, and visà versa.

When the pulse generator clock signal again goes low, the first P-channel FET 48 turns off and the clock circuit 60 increments the number coupled to the selector input of the demultiplexer 70. In response to the selector input advancing, the decoder 72 in FIG. 7 deactivates its Q1 output line and renders the Q2 output active. This change in decoder outputs causes transistor 79 to turn off and transistor 77 to become conductive. When the second P-channel FET 77 turns on, the positive charge on the second output capacitor 51 decays through the first electrode 13 of the cutaneous stimulator 11 and the user's skin to the ground plane electrode layer 19.

When the clock signals changed resulting in the positive stimulation charge being applied to the electrode, the multiplexer 32 was stepped to select the signal from the next bandpass filter 28. Therefore, while the second output capacitor 51 is decaying, the first output capacitor 37 is being charged for the stimulation of the next electrode 13. In this manner, the operation of the pulse generator 33 and demultiplexer 70 are repeated for each bandpass filter signal. When the thirty-two signals from all of the bandpass filters 29 have been selected, the multiplexer 32 and demultiplexer 70 are reset to select the first bandpass filter 29 and the first electrode 13 to continuously repeat the entire process.

As seen from the forgoing description, the operation of the present electro-tactile auditory system 10 breaks the sound detected by the microphone 26 into thirty-two bands, the respective amplitudes of which stimulate a different one of the electrodes of the cutaneous stimulator 11. Each stimulation consists of a pair of pulses, corresponding in magnitude to the intensity of the audio signal in the respective band. The user perceiving stimuli of different intensities at different parts of his arm is able to discern the nature of the sound and distinguish one sound from another.

Although the novel cutaneous stimulator has been described in terms of an auditory system, it has equal application to visual tactile systems in which the input signal is received from a video camera. In such an application of the present invention, the stimulator would have a greater number of electrodes arranged in a two dimensional array. Similarly, the multiplexer and demultiplexer circuits would be increased to accommodate the larger array of electrodes and appropriate clock signals would also be provided.

Furthermore, the present cutaneous stimulator can be employed with respect to other types of input signals than auditory or visual ones. For example, pressure sensors can be built into the fingers of the gloves of a protective suit to provide the wearer with an increased sense of touch. The stimulator can enhance the human senses by providing tactile stimulation to external stimuli which would otherwise be imperceptible by humans, such as ultra-sonic frequencies. The present invention can also be employed to stimulate muscles by the application of electricity.

While certain specific details have been described for the purpose of optimum presentation of the advantageous features of the invention, various modifications will be apparent to those skilled in the art without departing from the scope or spirit of the invention. For example, while the circuitry for the pulse generator and demultiplexer has been described in terms of individual components, off-the-shelf or custom integrated circuits, such as those for digital signal processing, can be adapted for the same functions. For example, the bandpass filter array 28, diodes 30 and multiplexer 32 could be replaced with a digital signal processor circuit from which the sound level in each of thirty-two bands is sequentially transmitted to the pulse generator 33. For example, the functions of these components could be achieved using a DSP56001 digital signal processing integrated circuit manufactured by Motorola. Likewise, the functions of the demultiplexer can be implemented by other types of digital signal processor integrated circuits, such as model DG 568 manufactured by Siliconix.

We claim:

1. A cutaneous stimulator for applying electricity to the skin of a user comprising:
   a flexible substrate upon one surface of which is formed a printed circuit pattern, the pattern including a plurality of electrodes and conductors connected to the electrodes;
   an insulating layer contiguous with the one surface of said substrate and having a plurality of apertures each of which is aligned with one of said electrodes; and
   an electrically conductive layer contiguous with said insulating layer and having a plurality of apertures therethrough each one of which being aligned with a different one of said electrodes.

2. The stimulator as recited in claim 1 further comprising a layer of a conductive material selected from the group consisting of titanium, gold, silver, graphite, and platinum, applied to an exposed surface of each of said electrodes.

3. The stimulator as recited in claim 1 further comprising means, attached to said substrate, for applying electricity to each of said electrodes.

4. The stimulator as recited in claim 1 further comprising means for producing a pair of electrical pulses of opposite polarities and for applying the pair of pulses to at least one of said electrodes, the magnitudes of the pulses having a relationship which does not produce a substantial change in the pH of the skin.

5. The stimulator as recited in claim 4 wherein the relationship between the magnitudes of the pulses is defined by a linear equation.

6. The stimulator as recited in claim 1 further comprising a separate layer of dielectric material contiguous with each of said electrodes.

7. The stimulator as recited in claim 6 wherein said dielectric material is an oxide of a metal.

8. The stimulator as recited in claim 7 wherein said oxide of a metal is selected from the group consisting of niobium oxide, titanium oxide, and tantalum pentoxide.

9. The stimulator as recited in claim 1 wherein said electrically conductive layer comprises a layer of a plastic impregnated with a conductive material.

10. The stimulator as recited in claim 1 wherein said electrically conductive layer comprises a graphite coating applied to said insulating layer.

11. The stimulator as recited in claim 1 further comprising another flexible substrate upon one surface of which is formed a printed circuit pattern including a plurality of conductors, the one surfaces of both substrates being adjacent each other with the conductors of each substrate being electrically coupled together.

12. The stimulator as recited in claim 11 wherein an adhesive coating attaches the two substrates, said adhesive coating having a resistance in the direction normal to the surfaces of the substrates which is relatively high in comparison to resistance in the directions parallel to the surfaces.

13. A cutaneous stimulator for applying electricity to the skin of a user comprising:
a substrate;
a plurality of first electrodes on said substrate;
a second electrode surrounding each of said first electrodes and electrically isolated therefrom;
means for applying to each of said first electrodes, a first charge pulse of one polarity followed by a second charge pulse of the opposite polarity, the absolute magnitude of the pulses of each polarity applied to a given electrode being unequal by a given amount so that the pH of the skin remains substantially unchanged by the application of the pulses to the electrodes.

14. The stimulator as recited in claim 13 wherein said means for applying includes:
a first means for producing an electric pulse of a first polarity,
a first capacitor coupled to said first means for producing an electric pulse to charge said first capacitor in response to the electric pulse of the first polarity;
a second means for producing an electric pulse of a second polarity having a absolute magnitude which is less than the absolute magnitude of the electric pulse of the first polarity;
a second capacitor coupled to said second means for producing an electric pulse to charge said second capacitor in response to the electric pulse of the second polarity; and
means for sequentially discharging said capacitors through one of said first electrodes.

15. The stimulator as recited in claim 14 wherein the electric pulse of said first polarity has a positive voltage and the electric pulse of said second polarity has a negative voltage.

16. The stimulator as recited in claim 14, wherein the absolute magnitude of the electric pulse of a first polarity has a predetermined relationship to the absolute magnitude of the electric pulse of a second polarity, which relationship is chosen so that the pH of the skin remains substantially unchanged by the application of the pulses to the electrodes.

17. The stimulator as recited in claim 16 wherein said means for applying is attached to said substrate.

18. The stimulator as recited in claim 13 wherein one of the electrical pulses has a rapid positive voltage level rise time with respect to a first interval of a subsequent voltage level decay, and the other electrical pulse has a rapid negative voltage rise time with respect to a second interval of subsequent negative voltage level decay.

19. A method for stimulating the skin employing a stimulator having a stimulation electrode and a ground electrode adjacent the stimulation electrode, both electrodes being in contact with the skin; the method comprising sequentially applying a pair of electrical pulses of opposite polarities to the stimulation electrode, the absolute magnitudes of the pulses being unequal and having a predefined relationship which does not produce a substantial change in the pH of the skin.

20. The method as recited in claim 19 wherein the relationship between the magnitudes of the pulses is defined by a linear equation.

21. The method as recited in claim 19 wherein one of the electrical pulses has a rapid positive voltage level rise time with respect to a first interval of a subsequent voltage level decay, and the other electrical pulse has a rapid negative voltage rise time with respect to a second interval of a subsequent negative voltage level decay.

* * * * *